United States Patent
Khursenko

(10) Patent No.: US 8,301,240 B2
(45) Date of Patent: Oct. 30, 2012

(54) SYSTEM FOR PROVISIONAL RADIO FREQUENCY CARDIAC STIMULATION FOR REPLACEMENT OF THE PACEMAKER

(75) Inventor: Vakeriy Khursenko, Kiev (UA)

(73) Assignee: Chamed SRL, Formello, Rome (IT)

( * ) Notice: Subject to any disclaimer, the term of this patent is extended or adjusted under 35 U.S.C. 154(b) by 18 days.

(21) Appl. No.: 12/599,231

(22) PCT Filed: May 9, 2008

(86) PCT No.: PCT/IB2008/051859
§ 371 (c)(1),
(2), (4) Date: May 26, 2010

(87) PCT Pub. No.: WO2008/139405
PCT Pub. Date: Nov. 20, 2008

(65) Prior Publication Data
US 2010/0305652 A1      Dec. 2, 2010

(30) Foreign Application Priority Data

May 11, 2007   (DE) .......................... 10 2007 022 084

(51) Int. Cl.
*A61N 1/00*    (2006.01)
(52) U.S. Cl. .......................................................... 607/2
(58) Field of Classification Search .................. 607/2
See application file for complete search history.

(56) References Cited

U.S. PATENT DOCUMENTS

| | | | |
|---|---|---|---|
| 5,782,892 A | 7/1998 | Castle et al. | |
| 6,947,792 B2 * | 9/2005 | Ben-Haim et al. | 607/2 |
| 7,519,424 B2 * | 4/2009 | Dennis et al. | 607/36 |

FOREIGN PATENT DOCUMENTS

| | | |
|---|---|---|
| EP | 0 603 137 A2 | 12/1992 |
| GB | 829 239 | 3/1960 |
| WO | 98/48897 A1 | 11/1998 |
| WO | 2006/008561 A1 | 1/2006 |

* cited by examiner

*Primary Examiner* — George Evanisko
*Assistant Examiner* — Nadia Ahmad
(74) *Attorney, Agent, or Firm* — Stradley Ronon Stevens & Young, LLP

(57) ABSTRACT

The present invention relates to a device for provisional cardiac stimulation during replacement of pacemakers (PMs). Said device enables fitting on an electrode catheter separated from the pocket of the PM of a radio-frequency coil (2) connected to an external apparatus (3) for generating variable-frequency pulsed signals. The device according to the invention can be used in the case of both unipolar and bipolar electrodes. According to a preferential embodiment, a sterile plate or electrode is set subcutaneously and connected to the external generator (3) for completing reclosing for cardiac stimulation, hi the event where there is the need to intervene in order to replace of a PM with bipolar electrodes, the subcutaneous plate is preferentially used; the subcutaneous plate is preferentially used as positive electrode, used RF stimulation will in this case be performed in a unipolar way by the combined action of the plate and of the electrode probe of the electrode catheter.

3 Claims, 1 Drawing Sheet

Figure 1:
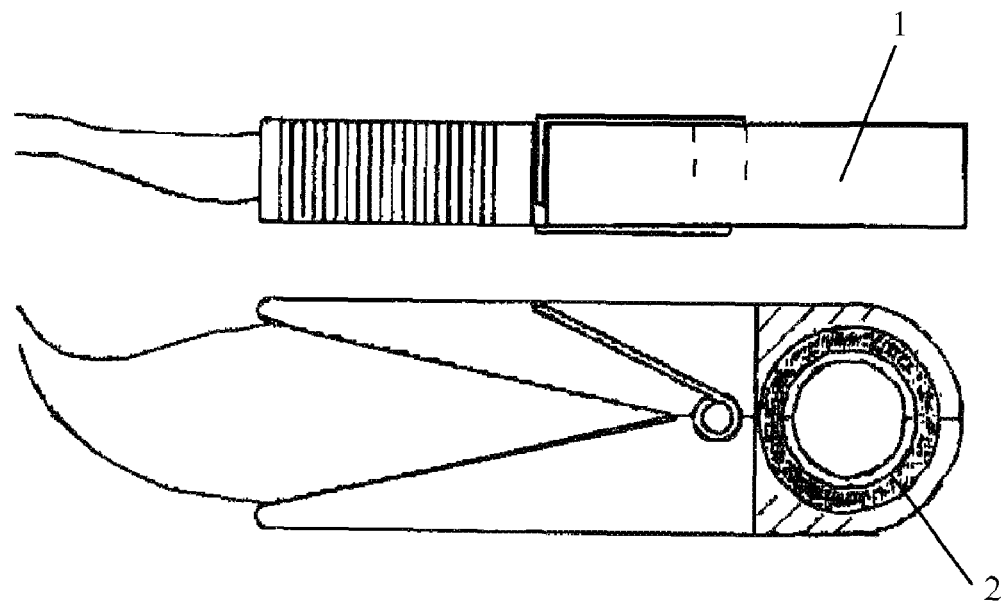

SYSTEM FOR PROVISIONAL RADIO FREQUENCY CARDIAC STIMULATION FOR REPLACEMENT OF THE PACEMAKER

FIELD OF THE INVENTION

The present invention falls within the framework of provisional cardiac stimulation during replacement of a pacemaker and regards more precisely systems for cardiac stimulation provided with a radio-frequency receiver designed to receive stimulation pulses alternative to those of the pacemaker, emitted by a radio-frequency transmitter external to the patient.

STATE OF THE ART

In systems normally used for provisional cardiac stimulation provided with radio-frequency (RF) receivers, the electrode that connects the pacemaker to the heart is unipolar, and fitted on said electrode is a radio-frequency receiver bearing on the outside of its casing a plate for contact with the tissues of the patient.

Also the pacemaker carries a plate for contact with the tissues of the patient and both in the case of stimulation by pacemaker and in the case of alternative stimulation by an external transmitter one of the polarities of the signal (normally the negative one) runs along the electrode whilst the other polarity (the positive one), is transmitted to the heart by the contact plates and traverses the tissues of the patient.

This current configuration presents some drawbacks both as regards operation of the stimulator and as regards the structure thereof, in particular of the radio-frequency receiver. The drawback regarding operation of current-stimulation systems lies in the fact that, on account of the high density of the current transmitted, undesirable muscular contractions may arise in the thorax of the patient.

In addition, a further drawback is represented by the fact that, during replacement of the pacemaker (PM), the aforesaid systems require direct contact with the electrode catheter, the connector of which is hence inevitably occupied. Said configuration, along with the primary need of not interrupting cardiac stimulation, renders logistically complicated both the operations of replacement of the PM and the necessary intra-operational measurements.

Described in EP603137 is a tool by means of which the connector of the electrode fitted on the pacemaker, which is rendered accessible from outside, can be pushed out of the PM; the tool is provided with means for contact with the electrode that make possible uninterrupted electrical stimulation of the heart throughout the operation of replacement of the PM. This type of tool cannot be used for those types of RF PMs in which it is desired to maintain stimulation with a programmed frequency during the intervention for replacement of the PM.

AIM OF THE INVENTION

On the basis of the drawbacks indicated above, a primary aim of the present invention is hence to provide a device that will enable the operator to intervene for a convenient replacement of the PM without occupying the connector of the electrode catheter and without causing absence of continuity of cardiac stimulation.

DESCRIPTION OF THE INVENTION

The aforesaid purpose is obtained via a device, as indicated in Claim 1, and the corresponding method of use, as defined in Claim 3.

The above device comprises the following parts:
a pressure clip (1);
an openable radio-frequency coil (2) mounted on the pressure clip (1); and
an external apparatus (3) for generating variable-frequency pulsed signals.

In addition, the device also envisages a subcutaneous sterile electrode connected to the external generator (3) for completing reclosing for cardiac stimulation.

Figure 2:
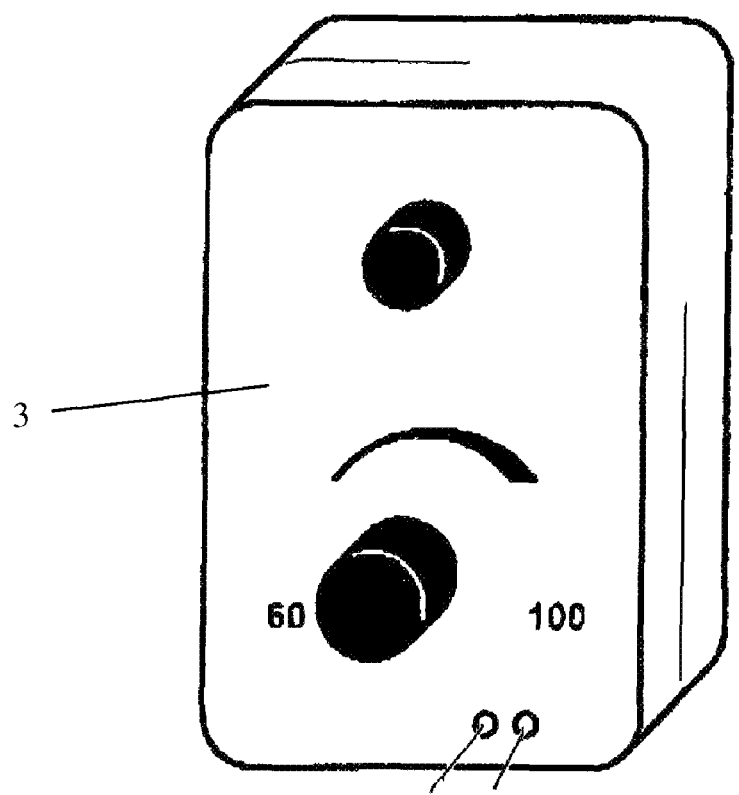

The invention will now be described in greater detail via the aid of the figures, wherein:

FIG. 1 is a front longitudinal view of a clip 1 with openable coil 2 according to the present invention; and FIG. 2 illustrates an external apparatus 3 for generating variable-frequency pulsed signals.

The idea underlying the present invention is to fit on an electrode catheter separated from the pocket of the PM a radio-frequency (RF) coil 2 connected to an external apparatus 3 for generating variable-frequency pulsed signals.

The fitting is made without altering the operative conditions of the electrode catheter itself, on which it will be possible to work without any hindrance. As soon as the PM has been replaced, the coil 2 can be easily and definitively removed. The coil 2 is in fact of the openable type, mounted on a pressure clip 1 that renders fitting and removal thereof immediate.

The variable electrical field generated within the coil generates on the circuit, which is formed by the electrode catheter and closes through the patient, a stimulation signal of variable frequency that can be regulated on the external apparatus.

Subcutaneous reclosing will be effected by means of an electrode that is supplied sterile and is connected to the external generator and anchored to the subcutis by means of a plate, which enables an increase in the surface of contact.

The device according to the present invention proves indispensable in all replacements of pacemakers (PMs), where it is necessary to maintain cardiac stimulation even for long periods before applying the new pacemaker. The operator after having separated the electrode catheter from the subcutaneous pocket, fits the clip around the electrode catheter itself in a simple way and without engaging the connector of the electrode catheter, which remains available for removal of the old PM and insertion of the new PM.

The plate described above positioned in the subcutis will complete reclosing for stimulation. By means of the regulation provided on the external apparatus it will be possible to stimulate at the desired frequency and proceed to the operations of replacement of the pacemaker. Once replacement is completed, it will be possible to remove the clip without interfering with the connections made.

The insertion of an external provisional RF stimulation as described herein thus provides an assurance for the operator, enabling simplicity and convenience of execution of both the operations of connection and the intra-operational measurements.

The invention claimed is:

1. A device for providing radio-frequency cardiac stimulation during replacement of a pacemaker (PM) comprising:
   a pressure clip, wherein the pressure clip is attachable to an electrode catheter;
   an openable radio-frequency coil mounted on the pressure clip;

an external apparatus for generating variable-frequency pulsed signals, wherein the radio-frequency coil is connected to the external apparatus; and a subcutaneous sterile electrode connected to the external apparatus for completing reclosing for cardiac stimulation.

2. A method of use of the device according to claim 1 for providing radio-frequency cardiac stimulation during replacement of the PM, comprising the following steps:

fitting the pressure clip of the device around the electrode catheter, wherein the electrode catheter connects the PM to a heart of a subject, wherein the electrode catheter is separated from a pocket of the PM, and wherein the fitting is made without engaging a connector of the electrode catheter during the replacement of the PM; and choosing a frequency of stimulation via the external.

3. The method according to claim 2, further comprising generating an the electrical field within the coil which generates a circuit, which is formed by the electrode catheter and closes through the subcutaneous electrode, a stimulation signal of variable frequency regulated by the external apparatus.

* * * * *